US009896392B2

(12) United States Patent
Meiswinkel et al.

(10) Patent No.: US 9,896,392 B2
(45) Date of Patent: Feb. 20, 2018

(54) METHOD FOR OLIGOMERIZATION OF ETHYLENE

(71) Applicants: SAUDI BASIC INDUSTRIES CORPORATION, Riyadh (SA); LINDE AG, Munich (DE)

(72) Inventors: Andreas Meiswinkel, Munich (DE); Wolfgang Mueller, Munich (DE); Anina Woehl, Munich (DE); Marco Harff, Munich (DE); Heinz Bolt, Wolfratshausen (DE); Karl-Heinz Hofmann, Germering (DE); Hans-Jorg Zander, Munich (DE); Anton Wellenhofer, Hohenschaftlam (DE); Abduljelil Iliyas, Riyadh (SA); Shehzada Khurram, Riyadh (SA); Shahid Azam, Riyadh (SA); Abdullah Al-Qahtani, Riyadh (SA)

(73) Assignees: SAUDI BASIC INDUSTRIES CORPORATION, Riyadh (SA); LINDE AG, Munich (DE)

( * ) Notice: Subject to any disclaimer, the term of this patent is extended or adjusted under 35 U.S.C. 154(b) by 0 days.

(21) Appl. No.: 14/414,403

(22) PCT Filed: Jun. 5, 2013

(86) PCT No.: PCT/EP2013/001658
§ 371 (c)(1),
(2) Date: Jan. 12, 2015

(87) PCT Pub. No.: WO2014/008964
PCT Pub. Date: Jan. 16, 2014

(65) Prior Publication Data
US 2015/0203418 A1 Jul. 23, 2015

(30) Foreign Application Priority Data
Jul. 10, 2012 (EP) .................... 12175732

(51) Int. Cl.
*C07C 2/36* (2006.01)
*B01J 31/14* (2006.01)
*B01J 31/18* (2006.01)

(52) U.S. Cl.
CPC .............. *C07C 2/36* (2013.01); *B01J 31/143* (2013.01); *B01J 31/187* (2013.01); *B01J 31/1885* (2013.01); *B01J 2231/20* (2013.01); *B01J 2531/62* (2013.01); *C07C 2531/14* (2013.01); *C07C 2531/24* (2013.01)

(58) Field of Classification Search
CPC .... B01J 31/143; B01J 31/187; B01J 31/1885; B01J 2531/62; B01J 2500/02; C07C 2/36; C07C 11/08; C07C 11/107; C07C 2531/14; C07C 2531/24; C08F 4/22; C08F 4/69; C08F 210/16; C08F 2500/02; Y02P 20/52
See application file for complete search history.

(56) References Cited

U.S. PATENT DOCUMENTS

| | | | |
|---|---|---|---|
| 4,020,121 A | 4/1977 | Kister | |
| 4,370,456 A | 1/1983 | George | |
| 4,721,762 A | 1/1988 | Commereuc | |
| 4,777,315 A | 10/1988 | Levine et al. | |
| 5,856,610 A | 1/1999 | Tamura et al. | |
| 8,076,524 B2 | 12/2011 | Lattner | |
| 2007/0185360 A1 | 8/2007 | Buchanan | |
| 2015/0299069 A1* | 10/2015 | Azam et al. | C07C 2/36 585/513 |

FOREIGN PATENT DOCUMENTS

| | | |
|---|---|---|
| CN | 101291893 A | 10/2008 |
| CN | 102387860 A | 3/2012 |
| EP | 1456153 A1 | 9/2004 |
| EP | 1777208 A1 | 4/2007 |
| EP | 2106854 A1 | 10/2009 |
| EP | 2239056 A1 | 10/2010 |
| EP | 2106854 | 5/2011 |
| EP | 2684857 A1 | 1/2014 |
| JP | H09143228 A | 6/1997 |
| JP | 2005533872 A | 11/2005 |
| JP | 2009527336 A | 7/2009 |
| JP | 2010532711 A | 10/2010 |
| JP | 2011504799 A | 2/2011 |
| JP | 2011518034 A | 6/2011 |

(Continued)

OTHER PUBLICATIONS

European Search Report, Application No. EP 12175732.2, dated Oct. 25, 2012; Client Ref. No. SL30007EP, 5 pages.
European Written Opinion, Application No. EP 12175732.2, dated Oct. 25, 2012; Client Ref. No. SL30007EP, 5 pages.
International Search Report; International Application No. PCT/EP2013/001658; dated Jun. 5, dated Jun. 11, 2013; Client Reference No. SL30007PCT; 5 pages.
Written Opinion of the International Searching Authority; International Application No. PCT/EP2013/001658; dated Jun. 5, 2013; dated Jun. 11, 2013; Client Reference No. SL30007PCT; 12 pages.

(Continued)

*Primary Examiner* — Nathan M Nutter
(74) *Attorney, Agent, or Firm* — Cantor Colburn LLP

(57) ABSTRACT

The present invention relates to a method for oligomerization of ethylene, comprising the steps:
a) feeding ethylene, solvent and a catalyst composition comprising catalyst and cocatalyst into a reactor,
b) oligomerizing ethylene in the reactor,
c) discharging a reactor effluent comprising linear alpha-olefins including 1-butene, solvent, unconsumed ethylene dissolved in the reactor effluent, and catalyst composition from the reactor,
d) separating ethylene and 1-butene collectively from the remaining reactor effluent, and
e) recycling at least a part of the ethylene and the 1-butene separated in step d) into the reactor.

20 Claims, 2 Drawing Sheets

(56) References Cited

FOREIGN PATENT DOCUMENTS

| | | |
|---|---|---|
| JP | 2012523306 A | 10/2012 |
| KR | 20110000559 A | 1/2011 |
| SU | 1387345 A1 | 11/1992 |
| WO | 03053890 A1 | 7/2003 |
| WO | 03053891 A1 | 7/2003 |
| WO | 2009006979 A2 | 1/2009 |
| WO | 2009068157 A1 | 6/2009 |
| WO | 2014008964 A1 | 1/2014 |

OTHER PUBLICATIONS

Zhiqiang Weng et al; Chromium (III) Catalysed Ethylene Tetramerization Promoted by Bis (Phosphino) Amines With an N-Functionalized Pendant, Dalton Transactions; Mar. 23, 2007, pp. 3493-3498, XP002685882, DOI: 10.1039/b702639f.

Russian Patent No. 1387345; dated Nov. 15, 1992; Machine Translation; 13 pages.

European Search Report, Application No. EP 12175732.2, Dated—Oct. 25, 2012; Client Ref. No. SL30007EP, 5 pages.

Written Opinion, Application No. EP 12175732.2, Dated—Oct. 25, 2012; Client Ref. No. SL30007EP, 5 pages.

International Search Report; International Application No. PCT/EP2013/001658; International Filing Date Jun. 5, 2013; Dated Jun. 11, 2013; Client Reference No. SL30007PCT; 5 pages.

Tao Jiang et al; The Effect of N-Aryl Bisphosphineamine Ligands on the Selective Ethylene Tetramerization; Journal of Molecular Catalysis A: Chemical, vol. 279, Oct. 16, 2007, pp. 90-93, XP002685883.

Written Opinion of the International Searching Authority; International Application No. PCT/EP2013/001658; International Filing Date Jun. 5, 2013; Dated Jun. 11, 2013; Client Reference No. SL30007PCT; 12 pages.

Zhiqiang Weng et al; Chromium (III) Catalysed Ethylene Tetramerization Promoted by Bis (Phosphino) Amines With an N-Functionalized Pendant, Dalton Transactions; Mar. 23, 2007, pp. 13493-3498, XP002685882, DOI: 10.1039/b702639f.

\* cited by examiner

METHOD FOR OLIGOMERIZATION OF ETHYLENE

CROSS-REFERENCE TO RELATED APPLICATION

This application is a National Stage Filing of International Application No. PCT/EP2013/001658; filed on Jun. 5, 2013, which claims priority to EP Patent Application No. 12175732.2; filed Jul. 10, 2012, both of which are incorporated herein by reference in their entirety.

BACKGROUND

The present invention relates to a method for the oligomerization of ethylene.

Methods for the oligomerization of ethylene using various catalyst compositions are well known in the art. Typically, if very unspecific catalysts are used, a broad product distribution is obtained from $C_4$ to higher olefins and even polymeric materials. Higher linear alpha-olefins and polymeric materials may cause plugging and fouling of the oligomerization reactor and pipings connected therewith. Recently, catalyst compositions for the oligomerization of ethylene have been developed which are more specific to, for example, trimerization or tetramerization, thus resulting in a narrower product distribution, but still also producing higher linear alpha-olefins and polymeric materials.

WO 2009/006979 A2 describes a process and a corresponding catalyst system for the di-, tri- and/or tetramerization of ethylene, based on a chromium complex with a heteroatomic ligand, typically featuring a PNPNH-backbone and activated by an organoaluminum compound such as, e.g., trialkylaluminum or methylaluminoxane. Among other possible embodiments of this invention, $CrCl_3(thf)_3$ (thf=tetrahydrofuran) is preferentially used as chromium source.

EP 2 239 056 A1 describes a catalyst composition and a process for oligomerization, in particular for the selective trimerization of ethylene to 1-hexene, using a modification of the catalyst system disclosed in WO 2009/006979 A2. While also relying on ligand types featuring the PNPNH-backbone, these modified systems show distinct advantages over the original catalyst compositions in terms of stability, activity, selectivity and the allowable window of operability concerning process parameters in a technical environment.

According to EP 2 239 056 A1, halogen-containing modifiers are used, in conjunction with, for example, $Cr(acac)_3$ (acac=acetylacetonate), the PNPNH-ligand and triethylaluminum as activator. Typical modifiers are, e.g., tetraphenylphosphonium- or tetraalkylammonium halides, preferentially the chlorides. In contrast to catalyst systems using $CrCl_3(thf)_3$ as chromium source, these modified systems allow for a free and independent adjustment of the chromium/halogen/aluminum ratio. This is a very advantageous strategy, since basic mechanistic investigations have shown that the halogen is an indispensable constituent of the catalytically active species, thus influencing the overall catalytic performance.

A typical oligomer product distribution of this above mentioned catalyst system is:

| C4 | 2.9 wt.-% |
| C6 | 91.4 wt.-% (>99.0 wt.-%) 1-hexene |
| C8 | 0.5 wt.-% |
| C10 | 5.1 wt.-% |
| ≥C12 | 0.1 wt.-% |

A typical process for a homogeneous catalyzed ethylene oligomerization technology of the prior art is shown in FIG. 1.

The homogeneous catalyst system 1 is transferred together with the solvent 2 (e.g. toluene) to the reactor 3. The linear alpha olefins, mainly 1-hexene, are formed via trimerization of dissolved ethylene in the liquid phase. Within the reactor the reaction heat of the exothermic reaction has to be removed and a fast phase transfer of the gaseous ethylene to the solvent has to be realized. Various reactor types are conceivable. Some examples are:

1. Bubble column reactor: to avoid internal heat exchange surfaces, ethylene can be used both as reaction feed and cooling medium. Simultaneously, mixing is achieved via the rising bubbles above a suitable sparger plate.
2. Loop reactor with external heat exchanger.
3. Plug-flow reactor: the reaction heat can be removed via the reactor wall.

A preferred reactor for the ethylene oligomerization is the bubble column reactor. Ethylene is introduced via a gas distribution system to the bottom section, whereas the liquid heavy LAOs, together with the solvent and the catalyst, are withdrawn from the bottoms. The oligomerization reaction is highly exothermic. By removing this heat with the ethylene, heat exchanger surfaces within the reaction area, which would be subject to heavy fouling, are avoided. A part of the formed linear a-olefins, which are gaseous under reaction conditions, are condensed at the top of the reactor and serve as reflux for cooling purpose, taking advantage from their respective heat of evaporation. Typical reaction conditions are: 30-70° C. at 10-100 bar.

After the reaction section the liquid product including the solvent (e.g. toluene) with the dissolved ethylene is fed to the separation section. In a first column 4 the unconsumed ethylene is separated from the product and the solvent. The ethylene is recycled back to the reactor via line 5. Ethylene polishing 6 may take place at line 5. The heavier fractions are routed to the subsequent separation 7 where they are divided into the different fractions (C4, C6, solvent, C8, C10, >C12). The solvent is recovered and recycled back to the reactor.

Starting with the class of very advantageous modified catalyst systems, as described, for example, in EP 2 239 056 A1, the question arises how an economic process for the oligomerization of ethylene, especially the selective trimerization of ethylene to 1-hexene, should be designed. The following challenges have to be considered in this regard:

1. The reaction heat from the exothermic reaction has to be removed from the reactor. Due to the fact that the catalyst is very sensitive against high temperatures, a reaction temperature preferably between 30 and 70° C. has to be maintained and controlled very precisely. Through the fact that small amounts of polyethylene are formed during the reaction, internal heat exchange surfaces show a tendency towards fouling. This leads inevitably to an unstable and/or unsafe operation of the reactor at only very limited times-on-stream. Therefore, such internal heat exchange surfaces should be avoided.
2. Unfortunately, formation of polymer or high molecular weight oligomers cannot be avoided completely during ethylene oligomerization, since this is an inherent side-reaction channel.

These solid materials may either be dissolved or suspended in the liquid product and, thus, finally be passed to the separation section or they may deposit in the inner surface of the reactor and its peripheral equipment. The latter is the worst case, since this may lead to fouling and plugging of the reactor. Consequently, the reactor and its associated equipment have to be cleaned periodically to remove the deposits. This leads to shutdowns and consequently to production loss. Consequently, polymer which is dissolved or suspended in the product stream is preferred.

SUMMARY

It is therefore an object of the present invention to provide a method for oligomerization of ethylene which overcomes the drawbacks of the prior art. Especially, the method shall be an economic process in terms of invest and operational costs and shall preferably provide stable and safe operation of the reactor with good heat removal and avoidance of plugging and fouling.

This object is achieved by a method for oligomerization of ethylene, comprising the steps:
a) feeding ethylene, solvent and a catalyst composition comprising catalyst and cocatalyst into a reactor,
b) oligomerizing ethylene in the reactor,
c) discharging a reactor effluent comprising linear alpha-olefins including 1-butene, solvent, unconsumed ethylene dissolved in the reactor effluent, and catalyst composition from the reactor,
d) separating ethylene collectively and 1-butene from the remaining reactor effluent,
e) recycling at least a part of the ethylene and the 1-butene separated in step d) into the reactor.

In a most preferred embodiment, there is a catalyst composition deactivation step between steps c) and d).

DETAILED DESCRIPTION

Figure 1:
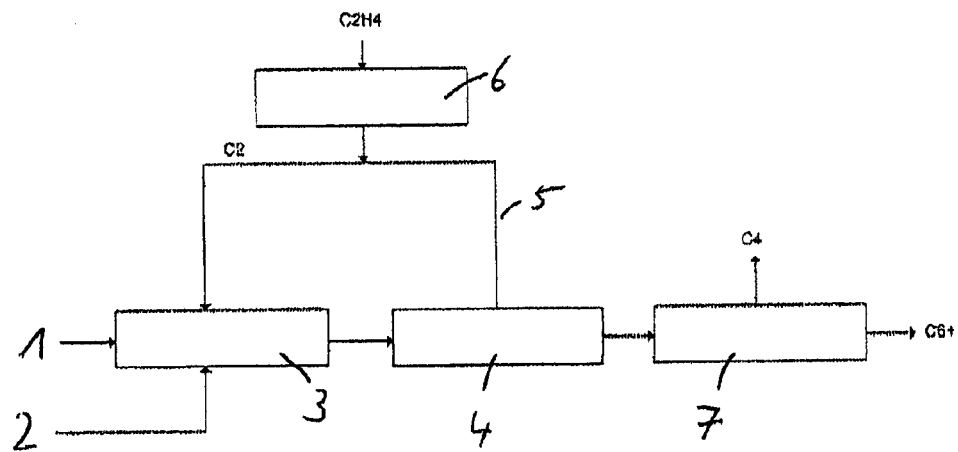
FIG. 1 illustrates a flow scheme for a conventional process for an ethylene oligomerization technology.

In principle, the total amount of ethylene, which is unconsumed, should be recycled back to the reactor with the goal to enhance the overall yield of the method. As it is preferred to adjust a constant 1-butene content during the method, a purge stream is then required. Consequently, through a purge a part of ethylene is discharged. Once a preferred 1-butene concentration in the liquid phase in the reactor is reached, the amount of 1-butene which is formed during the trimerization has to be purged. Due to the high selectivity, especially utilizing the trimerization catalyst as described below, the loss of ethylene through the purge is comparably low.

Preferably the reactor is a bubble column reactor.

Most preferably, the recycling stream of ethylene and 1-butene of step e) is purged at least partly by a purge stream.

In a most preferred embodiment, a steady state of the oligomerization is achieved, i.e. having a constant 1-butene content in the reactor. This constant 1-butene content can be achieved by respectively adjusting the amounts of 1-butene which are removed from the reactor with the reactor effluent and are recycled into the reactor in step e), and which amounts are purged from, preferably, the ethylene recycle.

In the steady state of the process, the whole amount of 1-butene, which is formed during oligomerization, has to be removed from the process. Otherwise, the 1-butene will accumulate further and the 1-butene concentration will increase. Due to the fact that there is only a C4/C6-split, the only possibility to remove the 1-butene from the process is to remove it with the ethylene in the recycle. In the steady state a constant amount of 1-butene is formed. This means that also a constant amount of the recycled stream has to be taken out. Consequently a part of the recycled stream has to be purged. The amount of the purged stream is in the steady state accordingly substantially constant. Through the amount of the purge stream the 1-butene concentration in the reactor and the composition of the purge stream can be adjusted. For example, in the case of a high purge stream the recycle consists mostly of ethylene and a lower amount of 1-butene, since a high amount of make-up/fresh ethylene is needed for the process. Consequently, less 1-butene is sent back to the reactor and higher amounts of a pure/fresh ethylene as make-up dilute the reactor composition. Hence, the concentration of 1-butene is lower. The contrary happens at a lower purge stream.

Due to the fact that the recycled stream can be gaseous as well as liquid, the purge stream can also be gaseous or liquid. The amount can be controlled by a mass flow controller. In the case that the recycled stream is condensed in a heat exchanger before it is sent back to the reactor, it might be energetically more beneficial to remove the purge stream before the recycle stream is condensed.

More preferably the amount of 1-butene in the reactor is at least 1 weight percent, more preferably 5 weight percent, more preferably 10 weight percent, more preferably 25 weight percent, based on the total weight of liquids in the reactor.

Even preferred 1-butene is present in the reactor in a maximum amount of 30 weight percent, based on the total weight of liquids in the reactor. In principle, even higher 1-butene contents are conceivable, such as a maximum amount of 50 or even 70 weight percent in the liquid phase, which contents are possible at a reaction pressure of 30 bar. In a most preferred embodiment, a steady state of the oligomerization is achieved in that equal amounts of 1-butene are removed from the reactor with the reactor effluent and are recycled into the reactor in step e).

Step b) may be preferably carried out at a temperature of 10-100° C., preferably 30-70° C., and/or a pressure of about 10-100 bar.

In one preferred embodiment, additional 1-butene is fed into the reactor, from an external source, preferably at an initial start-up period of the method for oligomerization.

Even preferred the separation of step d) is carried out at a pressure below reaction pressure of step b). In this embodiment, the product stream (reactor effluent) is depressurized before it is sent to a separation section. This has the advantage that the separation step can be enhanced. The investment and operational costs are reduced when the separation section (distillation column) is operated at a lower pressure. The $C_2+C_4$ product which is recycled back to the reactor has to be either recompressed to reaction pressure or it can be liquefied and pumped back to the reactor.

Ethylene and 1-butene may be advantageously recycled into the reactor in liquid form. The advantage of using a liquid recycle stream is that a pump can be used for the recycle stream instead of an expensive compressor. Simultaneously, the cooling capacity of the reactor is increased. Evaporation of the $C_2+C_4$ stream in the reactor removes a significant part of the exothermic reaction heat. Consequently, the ethylene gas recycle, which is necessary to cool the reactor, can be reduced. This is again beneficial for invest and operations costs of the method.

Preferably, the method for oligomerization is a trimerization to prepare thus substantially 1-hexene.

The catalyst composition may comprise a catalyst comprising a chromium compound and a ligand of the general structure (A) $R_1R_2P$—$N(R_3)$—$P(R_4)$—$N(R_5)$—H or (B) $R_1R_2P$—$N(R_3)$—$P(R_4)$—$N(R_5)$—$PR_6R_7$, wherein $R_1$-$R_7$ are independently selected from halogen, amino, trimethylsilyl, $C_1$-$C_{10}$-alkyl, $C_6$-$C_{20}$ aryl or any cyclic derivatives of (A) and (B), wherein at least one of the P or N atoms of the PNPN-unit or PNPNP-unit is a member of a ring system, the ring system being formed from one or more constituent compounds of structures (A) or (B) by substitution.

As is to be understood, any cyclic derivatives of (A) and (B) can be utilized as ligand, wherein at least one of the P or N atoms of the PNPN-unit (structure (A)) or PNPNP-unit (structure (B)) is a ring member, the ring being formed from one or more constituent compounds of structures (A) or (B) by substitution, i.e. by formally eliminating per constituent compound either two whole groups $R_1$-$R_7$ (as defined) or H, one atom from each of two groups $R_1$-$R_7$ (as defined) or a whole group $R_1$-$R_7$ (as defined) or H and an atom from another group $R_1$-$R_7$ (as defined), and joining the formally so-created valence-unsaturated sites by one covalent bond per constituent compound to provide the same valence as initially present at the given site.

Preferably the chromium compound is selected from organic or inorganic salts, coordination complexes and organometallic complexes of Cr(II) or Cr(III), preferably $CrCl_3$ $(THF)_3$, Cr(III)acetyl acetonate, Cr(III)octanoate, chromium hexacarbonyl, Cr(III)-2-ethylhexanoate, benzene(tricarbonyl)-chromium or Cr(III)chloride.

The co-catalyst may be selected from trimethylaluminum, triethylaluminum, triisopropylaluminum, triisobutylaluminum, ethylaluminumsesquichloride, diethylaluminumchloride, ethylaluminumdichloride, methylaluminoxane (MAO) or mixtures thereof. The catalyst composition may additionally comprise a modifier containing organic or inorganic halide.

More preferably the ligand may be selected from $Ph_2P$—N(i-Pr)—P(Ph)-N(i-Pr)—H, $Ph_2P$—N(i-Pr)—P(Ph)-N(Ph)-H, $Ph_2P$—N(i-Pr)—P(Ph)-N(tert-butyl)-H and $Ph_2P$—N(i-Pr)—P(Ph)-N(CH—(CH_3)(Ph))—H.

In principle, it is preferred that any of the catalyst compositions as disclosed in WO2009/006979 A2 or EP 2 239 056 A1, including any modifiers, can be successfully utilized, which are herewith incorporated by reference.

Finally the solvent may be selected from aromatic hydrocarbons, straight chain and cyclic aliphatic hydrocarbons, and ethers, preferably toluene, benzene, ethylbenzene, cumen, xylenes, mesitylene, hexane, octane, cyclohexane, methylcyclohexane, diethylether, tetrahydrofurane, and mixtures thereof, most preferably toluene.

Surprisingly it was found in the method of the present invention that 1-butene produced during the oligomerization can be successfully utilized as "co-solvent" to improve heat removal and removal of polymeric or high molecular weight compounds from the reactor.

In detail, since the amount of $C_4$ produced in an oligomerization reaction is usually comparably low, especially as a side reaction during ethylene trimerization, it was considered to design a separation section without a $C_2/C_4$ separation step. That means that after the reactor the liquid product (reactor effluent) is directly sent to a liquid $C_4/C_6$ separation column. While it is in principle conceivable to recycle only a part of the 1-butene back to the reactor, it is one of the main advantages of the present invention to safe one process step, namely the $C_2/C_4$-split. Consequently, to take this advantage, it is then necessary to recycle substantially the total amount of unconsumed ethylene and 1-butene prepared. Although some $C_4$ may end up in the $C_6$ fraction, which is not preferred due to negative impact on the 1-hexene quality, the purge stream, especially the purge rate, is the best option to adjust the 1-butene concentration in the reactor to optimum values. The heavier products, along with the solvent, are sent to the subsequent separation section as usual, where the solvent is recovered and the main product, 1-hexene, is separated.

It is clear for someone skilled in the art that in a very preferred embodiment, there is a catalyst deactivation step between steps c) and d) of the inventive method. Usually, for these purposes, after discharging the reactor effluent from the reactor, a deactivation agent is added to the product/toluene/catalyst solution. All established/disclosed deactivation methods are conceivable for this catalyst system: alcohol, water, caustic, air/$O_2$, amine, $CO/CO_2$. It is important that the deactivation agent is added in molar stoichiometric rates with respect to the catalyst and the co-catalyst, i.e. for example Cr-catalyst and aluminum alkyl activator, i.e. [Cat]+[Cocat]. This ensures a complete deactivation of the catalyst. Otherwise side-reactions in separation columns, for example olefin isomerization, are possible. The most preferred deactivation agent is a long-chain alcohol, especially 1-decanol, which after separation does not end up in the desired product 1-hexene fraction or the solvent.

Moreover, a mixture of 1-butene and ethylene is recycled back to the reactor from the light product of first separation step (the C4/C6 column) The recycled stream can be injected/distributed from the top of the reactor through a distributor plate or a nozzle. Alternatively, it can be also injected from the side into the fluid bed. The effect is that 1-butene, which is formed as by-product during the trimerization reaction (1-4 wt.-%), is accumulated in the reactor. Consequently, a significant amount of the liquid reactor phase mixture is 1-butene. This amount may vary from 1-30 wt.-%, compared to only 1-4 wt.-% net production.

Since 1-butene is usually a by-product of the oligomerization reaction, especially trimerization, it has to be discharged from the process. Therefore a purge stream may be required. The purge stream may consist preferably of between 10 and 90 wt.-% 1-butene while the rest of the stream is mainly ethylene. The purge stream can be sent back, for example, to a steam cracker where ethylene and 1-butene can be recovered. For the case that no cracker is available, this stream can be sold separately or used energetically. Depending on the situation, the purge stream can be used as fuel for boilers. Due to the fact that the catalyst produces very selectively 1-hexene with only a small amount of 1-butene as by-product, the loss of ethylene via the purge is comparably low.

The high 1-butene content in the reactor has a significant benefit for the removal of the reaction heat. By means of the recycle, gaseous ethylene and evaporated 1-butene is condensed and recycled back to the reactor. Therefore, the enthalpy of evaporation of 1-butene is used for the heat removal. Consequently, the gaseous ethylene stream, which also serves as cooling medium, can be reduced.

Interestingly, numerous laboratory experiments show that the catalyst system is very selective with respect to the substrate ethylene. This means that, despite the high amount of 1-butene in the liquid phase, the catalytic activity, the 1-hexene selectivity and the purity of 1-hexene are not affected. This is especially surprising, since mechanistic knowledge regarding the underlying metallacycle mechanism implies a certain chance of deteriorating 1-hexene selectivities if high concentrations of 1-butene are present in the reaction mixture. However such a detrimental effect is totally avoided here as a direct consequence of the very high selectivity of the catalytically active species, largely brought about by the preferred ligand featuring the PNPNH-backbone.

It is even more surprising that the high 1-butene content in the reactor changes advantageously the polymer mobilization behavior. This means that a significant portion of polymer that normally stays in the reactor as sticking layer on the internal reactor surfaces is now dissolved and suspended in the product stream. This means that at higher 1-butene concentrations in the reactor, a larger amount of side—product polyethylene is discharged along with the product.

In the subsequent examples it becomes obvious that higher C4 contents in the reaction mixture lead to better polymer mobilization and more of this unwanted material is discharged along with the liquid product. Obviously, high 1-butene concentrations lead to the formation of small polymer flakes, which have a lower affinity to accumulate and precipitate on the reactor wall or internals. Agglomeration of polyethylene particles is largely prevented by the improved solvent properties leading to a smaller particle size distribution. Thus, the reactor runtime until the reactor has to be cleaned can be extended by increasing the steady-state 1-butene concentration.

It is conceivable that the high concentration of light olefin changes the solvent properties. In principle, a new solvent (solvent+1-butene) with significantly improved solvent properties is now used in the reaction section. This changed solvent characteristics support the formation of smaller particles, which are better suspended in the liquid.

In summary, using a high 1-butene content in the liquid phase, the reactor cooling capacity can be enhanced significantly. By means of a recycle, where 1-butene rich gas phase is condensed and recycled to the reactor, the enthalpy of evaporation of 1-butene can be used for cooling. Consequently, the gaseous ethylene stream, which also serves as cooling medium, can be reduced. This is beneficial since lower recompression and cooling requirements are necessary.

No thermal heat exchange surfaces in the liquid reactor phase are necessary, since the reactor cooling can be achieved through evaporation of 1-butene and through the injection of cool ethylene.

The invest cost can be reduced, as through the inventive concept the distillation column for the $C_2/C_4$-split is not needed any longer. Also, the ethylene recycle equipment is smaller.

Reactor run times can be extended. Due to the better mobilization of the by-product polymer, the reactor fouling is reduced. Consequently, the interval before the reactor has to be cleaned again is extended.

Finally, due to the high 1-butene content, the process stability against thermal runaways is improved. An increasing reaction temperature causes a higher amount of 1-butene to evaporate, thus removing more heat. Consequently, the system is somewhat self-inhibiting to certain extent.

Additional features and advantages of the inventive method can be taken from the following detailed description of a preferred embodiment in connection with the drawings, wherein According to FIG. 1, illustrating a conventional process scheme for the oligomerization of ethylene, catalyst, solvent and ethylene are fed to a reactor where oligomerization, for example trimerization takes place. A liquid reactor effluent comprising solvent, unreacted ethylene, linear alpha-olefins and catalyst, is transferred to a first separation section where ethylene is separated. This ethylene can be recycled back to the reactor, the recycling cycle may comprise ethylene polishing. The heavier fractions are routed to a second and further separation sections where separation into different fractions, such as $C_4$, $C_6$, solvent, $C_8$, $C_{10}$, $>C_{12}$, is effected.

Figure 2:
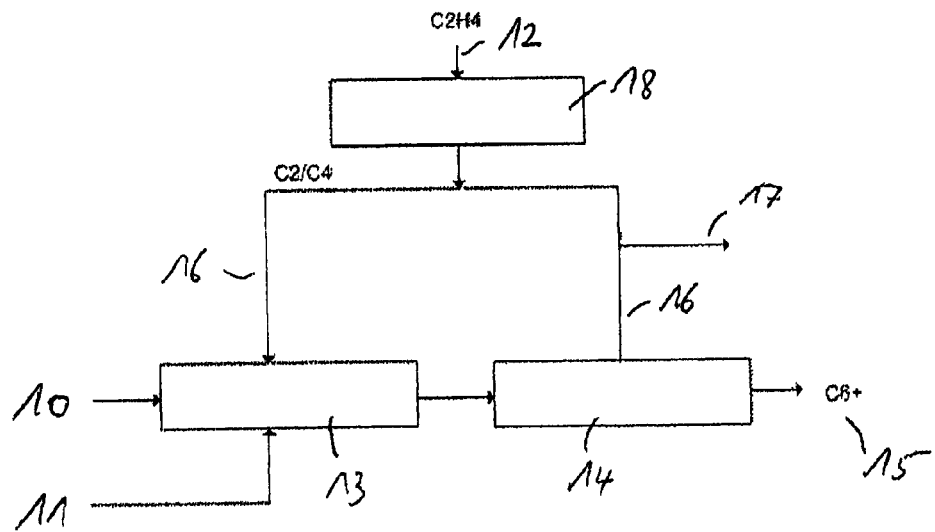
FIG. 2 shows a scheme for an ethylene oligomerization technology according to the present invention.

According to the inventive method, which is illustrated in FIG. 2, catalyst 10, solvent 11 and ethylene 12 are also fed to a reactor 13 for oligomerization, for example trimerization, of ethylene. In contrast to the method of the prior art, the reactor effluent is directly sent to a $C_4/C_6$ separation section 14 wherein both ethylene and $C_4$ are separated from the remainder. Ethylene and $C_4$ (at least partly) are recycled into the reactor via line 16. The recycle step may include a purge stream 17 and polishing 18 of ethylene. As in the prior art, the heavier fractions can be transferred to further separation sections 15.

EXAMPLES

A 300 ml pressure reactor, equipped with dip tube, thermowell, gas entrainment stirrer, cooling coil, control units for temperature, pressure, and stirrer speed (all hooked up to a data acquisition system) was inertized with dry argon. The isobaric ethene supply was maintained by an aluminum pressurized gas cylinder on a balance to monitor the ethene consumption over time by means of a computerized data acquisition system.

Before conducting an experiment, the reactor was heated to 100 C at reduced pressure for several hours to eliminate traces of water, oxygen and oxygenated impurities. Before the reaction the reactor was cooled down to the reaction temperature of 50° C.

For the catalyst preparation, suitable amounts of PNPNH-ligand (14.7 mg $(Ph)_2P—N(^iPr)—P(Ph)-N(^iPr)—H$, Ph=phenyl, iPr=isopropyl), chromium precursor $(Cr(acac)_3$, 10.5 mg) and modifier dodecycltrimethylammonium chloride $(CH_3(CH_2)_{11}N(CH_3)_3Cl$, 63.5 mg) were weighed in and charged to a Schlenk tube under inert atmosphere. A volume of 50/100 ml anhydrous toluene was added and the solution was stirred by means of a magnetic stirrer. After dissolving the Cr-compound, the ligand and the modifier, the required amount of a 93 wt.-% triethylaluminum ($AlEt_3$, 100 µl) was added. The solution was immediately transferred to the reactor.

The chosen volumes and masses correspond to a chromium concentration of 0.3/0.6 mmol/l at a molar ligand to chromium ratio of 1.2 mol/mol, an Al/Cr—ratio of 24 mol/mol and a Cl/Cr—ratio of 8 mol/mol.

To investigate the effect of accumulated gas in the ethylene recycle, the existing test rig was extended by a 2 l-gas cylinder. For a good quantification this cylinder was stored on a balance. The desired amount of 1-butene was filled into the reactor shortly before the reaction was started. After filling in, the stirrer was turned on and the ethylene supply was opened and the reactor was pressurized to 30 bar ethylene. Ethylene was fed on demand to hold the pressure constant at 30 bar. The ethylene consumption was monitored by the data acquisition system and an electronic balance by constantly weighing the ethylene pressure cylinder. The total amount of dosed 1-butene was determined via quantification and characterization of the gaseous and liquid product by GC-FID and the weight loss of the balance. The weight content of 1-butene in the liquid phase was calculated using the process simulation tool UniSim.

Following this procedure, a series of trimerization reactions was conducted with different amounts of 1-butene and different volumes of toluene to adjust different ratios of toluene/1-butene mixtures.

After the residence time of 1 h, the reaction in the liquid phase was quenched by transferring the liquid inventory by means of the ethylene pressure to a glass vessel filled with approx. 100 ml water. The mass balance of the experiment was determined via quantification and GC-FID analysis of the gaseous and liquid product separately, followed by comparison with the ethene uptake data. Based on the measured data, the overall yields and selectivities were determined.

The results of the experiments are summarized in Table 1.

TABLE 1

Experimental Standard performance tests with different amounts of 1-butene (Conditions: 50° C., 30 bar, 1 h)

| Entry. | Mass 1-C4 [g] | Initial 1-C4 content in the liquid[1) [wt.-%] | Average Activity [kg/($g_{Cr}$ * h)] | Selectivity [wt.-%] | | |
|---|---|---|---|---|---|---|
| | | | | C6 | 1-C6 | C10 |
| 1 | 0 | 0 | 39.0 | 91.4 | 99.1 | 5.1 |
| 2 | 3.2 | 3.2 | 39.5 | 93.2 | 99.0 | 4.5 |
| 3 | 2.5 | 2.5 | 34.9 | 93.9 | 99.0 | 4.4 |
| 4 | 5.0 | 4.9 | 37.5 | 94.3 | 99.0 | 4.3 |
| 5[2)] | 0 | 0 | 35.8 | 91.0 | 99.0 | 4.6 |
| 6[2)] | 6.6 | 11.8 | 41.0 | 92.3 | 99.0 | 4.8 |
| 7[2)] | 6.2 | 11.2 | 36.8 | 93.0 | 99.0 | 4.4 |
| 8[2)] | 18.0 | 26.0 | 39.4 | 93.2 | 98.9 | 4.2 |

[1)]The initial 1-C4 weight ratio was determined by UniSim (50/100 ml toluene with additional mass of 1-butene, saturated with ethylene at 30 bar, 50° C.)
[2)]$V_{toluene}$ = 50 ml, [Cr] = 0.6 mmol/l Surprisingly, the 1-hexene yield is very high, despite of the higher content of 1-butene in the liquid. Also the 1-hexene purity, which means the 1-C6 content in the C6 fraction, remains at 99.0 wt.-%, unaffected by high 1-butene concentrations. These results show the extraordinary selectivity of the homogeneous ethylene trimerization catalyst, favoring by far the incorporation of the ethylene feedstock into the product over the analogous reaction with 1-butene.

Figure 3:
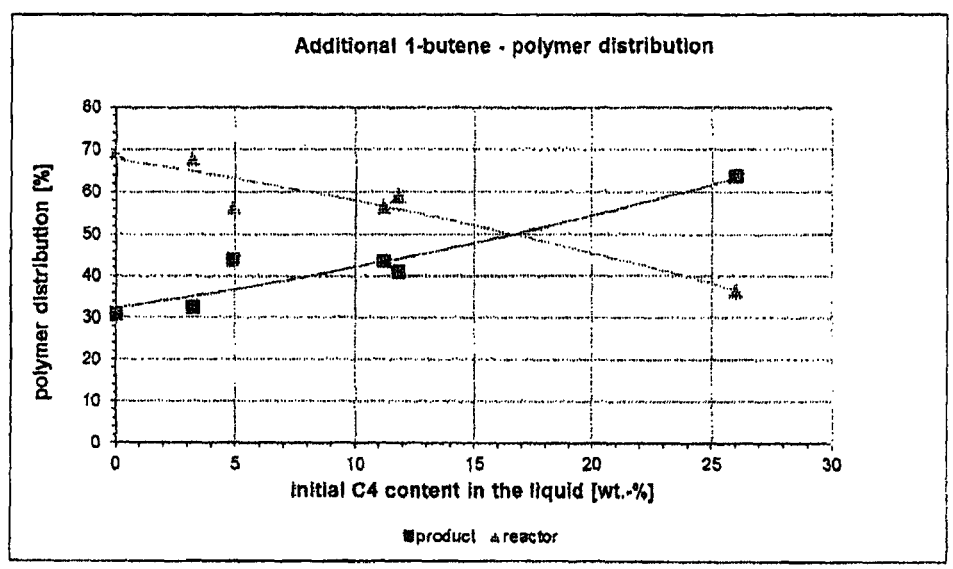
FIG. 3 illustrates a graph showing polymer distribution dependent on the initial $C_4$ in the liquid phase.

But interestingly and surprisingly the polymer mobilization behaviour changes significantly with the 1-butene concentration in the liquid phase. As shown in FIG. 3 it becomes obvious that at a high C4 content, the polymer is better mobilized and is discharged from the reactor along with the liquid product.

The features disclosed in the foregoing description, in the claims and in the accompanying drawings may, both separately and in any combination thereof, be material for realizing the invention in diverse forms thereof.

What is claimed is:

1. A method for oligomerization of ethylene, comprising the steps:
   a) feeding ethylene, solvent and a catalyst composition comprising catalyst and cocatalyst into a reactor,
   b) oligomerizing ethylene in the reactor,
   c) discharging a reactor effluent comprising linear alpha-olefins including $C_{6+}$ linear alpha olefins and 1-butene, solvent, unconsumed ethylene dissolved in the reactor effluent, and catalyst composition from the reactor,
   d) separating ethylene and 1-butene collectively from the remaining reactor effluent comprising the $C_{6+}$ linear alpha olefins, and
   e) recycling at least a part of the ethylene and the 1-butene separated in step d) into the reactor; and
   wherein a constant 1-butene content is in the reactor.

2. Method according to claim 1, wherein the recycling stream of ethylene and 1-butene of step e) is purged at least partly by a purge stream.

3. The method according to claim 1, wherein step b) is carried out at a temperature of 10-100° C. and/or a pressure of about 10-100 bar.

4. The method according to claim 1, wherein additional 1-butene is fed into the reactor, from an external source at an initial start-up period of the method for oligomerization.

5. The method according to claim 1, wherein the separation of step d) is carried out at a pressure below reaction pressure of step b).

6. The method according to claim 1, wherein ethylene and 1-butene are recycled into the reactor in liquid form.

7. The method according to claim 1, which is a trimerisation.

8. The method according to claim 1, wherein the catalyst composition comprises a catalyst comprising a chromium compound and a ligand of the general structure (A) $R_1R_2P$—$N(R_3)$—$P(R_4)$—$N(R_5)$—H or (B) $R_1R_2P$—$N(R_3)$—$P(R_4)$—$N(R_5)$—$PR_6R_7$, wherein $R_1$-$R_7$ are independently selected from halogen, amino, trimethylsilyl, $C_1$-$C_{10}$-alkyl, $C_6$-$C_{20}$ aryl or any cyclic derivatives of (A) and (B), wherein at least one of the P or N atoms of the PNPN-unit or PNPNP-unit is a member of a ring system, the ring system being formed from one or more constituent compounds of structures (A) or (B) by substitution.

9. The method according to claim 8, wherein the chromium compound is selected from organic or inorganic salts, coordination complexes and organometallic complexes of Cr(II) or Cr(III).

10. The method according to claim 1, wherein the co-catalyst is selected from trimethylaluminum, triethylaluminum, triisopropylaluminum, triisobutyl-aluminum, ethylaluminumsesquichloride, diethylaluminumchloride, ethylaluminumdichloride, methylaluminoxane (MAO) or mixtures thereof.

11. The method according to claim 1, wherein the catalyst composition additionally comprises a modifier containing organic or inorganic halide.

12. The method according to claim 8, wherein the ligand is selected from $Ph_2P$—N(i-Pr)—P(Ph)—N(i-Pr)—H, $Ph_2P$—N(i-Pr)—P(Ph)—N(Ph)-H, $Ph_2P$—N(i-Pr)—P(Ph)—N(tert-butyl)-H and $Ph_2P$—N(i-Pr)—P(Ph)—N(CH($CH_3$)(Ph))—H.

13. The method according to claim 1, wherein the solvent is selected from aromatic hydrocarbons, straight chain and cyclic aliphatic hydrocarbons, and ethers.

14. The method according to claim 13, wherein the solvent is selected from toluene, benzene, ethylbenzene, cumene, xylenes, mesitylene, hexane, octane, cyclohexane, methylcyclohexane, diethylether, tetrahydrofurane, and mixtures thereof.

15. The method according to claim 13, wherein the solvent is toluene.

16. The method according to claim 1, wherein the amount of 1-butene in the reactor is at least 5 percent, based on the total weight of liquids in the reactor.

17. The method according to claim 1, wherein the amount of 1-butene in the reactor is at least 10 percent, based on the total weight of liquids in the reactor.

18. The method according to claim 1, wherein the amount of 1-butene in the reactor is at least 25 percent, based on the total weight of liquids in the reactor.

19. The method according to claim 8, wherein the chromium compound is $CrCl_3(THF)_3$, Cr(III)acetyl acetonate, Cr(III)octanoate, chromium hexacarbonyl, Cr(III)-2-ethylhexanoate, benzene(tricarbonyl)-chromium or Cr(III)chloride.

20. The method according to claim 1, wherein the amount of 1-butene in the reactor is at least 1 weight percent and up to 30 weight percent, based on the total weight of liquids in the reactor.

* * * * *